US006232478B1

(12) United States Patent
Byun et al.

(10) Patent No.: US 6,232,478 B1
(45) Date of Patent: May 15, 2001

(54) PROCESS FOR THE PREPARATION OF CHIRAL 3,4-EPOXYBUTYRIC ACID AND THE SALT THEREOF

(76) Inventors: Il Suk Byun, 108-602, Hanmaroo Apt., 1388, Doonsan-dong, Su-ku, Taejeon, 302-173; Kyung Il Kim, 108-504 Sejong Apt., 462-5 Junmin-dong, Yusung-ku, Taejeon, 305-390; Yoon Hwan Choi, 1412-806, Maehwajookong Apt., Sanbon-dong, Kunpo, Kyungki-do, 435-040, all of (KR)

( * ) Notice: Subject to any disclaimer, the term of this patent is extended or adjusted under 35 U.S.C. 154(b) by 0 days.

(21) Appl. No.: 09/462,810
(22) PCT Filed: Jun. 17, 1998
(86) PCT No.: PCT/KR98/00166
§ 371 Date: Jan. 14, 2000
§ 102(e) Date: Jan. 14, 2000
(87) PCT Pub. No.: WO99/03850
PCT Pub. Date: Jan. 28, 1999

(30) Foreign Application Priority Data

Jul. 16, 1997 (KR) .................................................. 97/33208
Nov. 3, 1997 (KR) .................................................. 97/57812

(51) Int. Cl.$^7$ .................................................. C07D 301/02
(52) U.S. Cl. .................................................. 549/519; 549/518
(58) Field of Search ..................... 549/518, 519

(56) References Cited

U.S. PATENT DOCUMENTS

| 5,292,939 | 3/1994 | Hollingsworth | 562/515 |
|---|---|---|---|
| 5,319,110 | 6/1994 | Hollingsworth | 549/323 |
| 5,374,773 | 12/1994 | Hollingsworth | 562/515 |

FOREIGN PATENT DOCUMENTS

| 0 237 983 | 9/1987 | (EP) | C12P/17/02 |
|---|---|---|---|
| 03167167 | * 7/1991 | (JP) | C07C/309/65 |

OTHER PUBLICATIONS

G.A. Buscaino et al., "Prime Esperienze Clinche Ed Elettroencefalografiche Sulla Efficacia Antiepilettica Del Gabob E Dell'Elipten", Acta Neurologica, Anno XVI, N. 6, pp. 748–773, (1961).

D. DeMaio et al., "Gli Acidi Gamma–Aminobutirrico (GABA) E Gamma–Amino–Beta–Idrossibutirrico (GABOB) Nella Prospettiva Di Una Terapia Biologica Anticomiziale", Acta Neurologica, Anno XVI, N. 4, pp. 366–407, (1961).

M. Otsuka et al., "Measurement of $_\gamma$–Aminobutyric Acid in Isolated Nerve Cells of Cat Central Nervous System", Journal of Neurochemistry, vol. 18, pp. 287–295, (1971).

K. Ushikubo, "The Inhibitory Action of $_\gamma$–Amino–β–Hydroxy Butyric Acid on Seizure Following Electric Stimulations of Motor Area", J. Physiol. Soc. Japan, vol. 21, pp. 616–621, (1959).

B.E. Rossiter et al., "Asymmetric Epoxidation of Homoallylic Alcohols. Synthesis of (−)–γ–Amino–β(R)–Hydroxybutyric Acid (GABOB)", J. Org. Chem., vol. 49, pp. 3707–3711, (1984).

P. Mohr et al., "3–Hydroxyglutarate and β,γ–Epoxy Esters as Substrates for Pig Liver Esterase (PLE) and α–Chymotrypsin", Helvetica Chimica Acta, vol. 70 (1987) p. 143–152.

M. Larchevêque et al., "Préparation De Nouveaux Synthons Chiraux: Les β,γ–Époxyesters; Application À La Synthése De β–Hydroxyesters Énantiomériquement Purs", Tetrahedron Letters, vol. 28, No. 16, pp. 1781–1782, (1987).

M. Larchevêque et al., "Enantiomerically Pure β–γ–Epoxyesters from β–Hydroxylactones: Synthesis of β–Hydroxyesters and (−)–GABOB", Tetrahedron, vol. 46, No. 12, pp. 4277–4282, (1990).

* cited by examiner

Primary Examiner—Rosalynd Keys

(57) ABSTRACT

The present invention relates to a process for the preparation of chiral 3,4-epoxybutyric acid expressed by formula (1) and the salt thereof, wherein (S)-3-activated-hydroxybutyrolactone expressed by formula (2) is subjected to a ring-opening reaction to obtain 4-hydroxy-3-activated hydroxybutyric acid expressed by formula (3), which is subjected to an epoxydation with an inversion of the chiral center.

18 Claims, No Drawings

PROCESS FOR THE PREPARATION OF CHIRAL 3,4-EPOXYBUTYRIC ACID AND THE SALT THEREOF

BACKGROUND OF THE INVENTION

1. Field of the Invention

The present invention relates to the process for the preparation of chiral 3,4-epoxybutyric acid and the salt thereof expressed by the following formula 1, wherein (S)-3-activated hydroxybutyrolactone as a raw material and other inexpensive reactants are utilized so as to undergo an efficient ring-opening reaction and epoxydation with an inversion of chiral center.

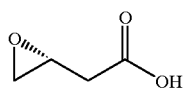
(1)

2. Description of the Prior Art

Chiral 3,4-epoxybutyric acid of formula 1 or the ester compound thereof is an useful raw material for the preparation of various chiral compounds due to the synthetic utility of the epoxy group. For example, (R)4-amino-3-hydroxybutyrolactone (GABOB) prepared from (R)-3,4-epoxybutyric acid is widely known for its use as an anti-epileptic or hypotensive drug [Otsuka, M., Obata. K., Miyata, Y., Yaneka, Y., J. Neurochem. (1971) 18, 287; Buscaino, G., A., Ferrari, E., Acta Neurol. (1961) 16, 748; DeMaio, D., Madeddu, A., Faggioli, L., Acta Neurol. (1961) 16, 366; Ushinkoba, K., Nippon Seirigaku Zassni (1959) 21, 6161.

The examples for the preparation of chiral (R)-3,4-epoxybutyric acid in the prior art are as follows: In the case of the process through the oxidation reaction after stereoselectively introducing the epoxy group via asymunetric epoxydation reaction U. Org. Chem., vol. 49, 3707~3711 (1984)], the low yield of 11~25% and stereo-selectivity of 55% ee result therefrom, which is rather problematic for the industrial purpose.

Another method is selectively obtaining (R)-3,4-epoxybutyric acid ester with the target chiral center by performing a biological optical resolution on the racemic 3,4-epoxybutyric acid ester, which in turn can be obtained via chemical method [Helvetical Chimica Acta, vol. 70, 142~152(1987); Europe Patent 237,983(1987)]. In the case above, the stereo-selectivity is superior. However, the reaction time of approximately 24 hours is required, and the yield of more than 50% cannot be expected as is the characteristic of the biological optical resolution reaction.

On the other hand, the method of preparing (S)-3,4-epoxvbutyric acid ethyl ester from (S)-3-hydroxybutyrolactone, or preparing (R)-3,4-epoxybutvric acid ethyl ester from (R)-3-hydroxybutyrolactone is well known [Larcheveque, M., Henrot, S., Tetrahedron Letters, (1987) 28, 1781; Larcheveque, M., Henrot, S., Tetrahedron, (1990) 46, 4277]. However, iodotrimethyl silane and silver oxide are rather expensive, and difficult anhydrous condition is required therein.

The optically pure 3-hydroxybutyrolactone has seldom been utilized as a chiral raw material in the past due to the difficulty in its preparation. But, recently, the very inexpensive and facile method of preparing (S)-3-hydroxybutyrolactone through oxidation and successive cyclization from inexpensive natural D-carbohydrates and hydrogen peroxide has been developed (U.S. Pat. Nos. 5,292,939, 5,319,110, 5,374,773). As a result, (S)-3-hydroxybutyrolactone is being utilized as a pivotal raw material in the preparation of various chiral compounds, and the extent of its use will be expanded.

SUMMARY OF THE INVENTION

As a result of intensive studies, the present invention has been devised in which (R)-3,4-epoxybutyric acid and the salt thereof can be economically prepared with inexpensive reagents. Under said invention, (S)-3-activated hydroxybutyrolactone as a raw material undergoes an inversion of the chiral center via ring-opening and epoxydation reactions. The inversion reaction of the chiral center with respect to the preparation of chiral 3,4-epoxybutyric acid has not been mentioned in the references. Generally, in the case of the chiral compound, both (S)- and (R)-types are useful as shown in [Larcheveque, M., Henrot, S., Tetrahedron Letters, (1987) 28, 1781; Larcheveque, M., Henrot, S., Tetrahedron, (1990)46, 4277]. In this respect, the above method is an useful reaction in which both (S)- and (R)-types of derivatives can be easily and efficiently prepared from (S)-3-hydroxybutyrolactone.

Consequently, the objective of the present invention is to prepare pure chiral 3,4-epoxybutyric acid with high yield, using relatively inexpensive and easily-handled compounds.

DETAILED DESCRIPTION OF THE INVENTION

The present invention relates to the process of preparing 3,4-epoxybutyric acid of the following formula 1, wherein (S)-3-activated hydroxybutyrolactone of the following formula 2 is subjected to a ring-opening reaction in the aqueous solvent, based on the above reaction, 4-hydroxy-3-activated hydroxybutyric acid of the following formula 3 is prepared therefrom, and 4-hydroxy-3-activated hydroxybutyric acid of said formula 3 is subjected to an inverse conversion reaction at the chiral center in the presence of a base for the preparation of 3,4-epoxybutyric acid of the following formula 1.

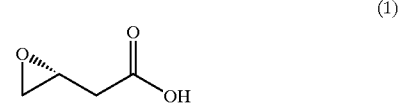
(1)

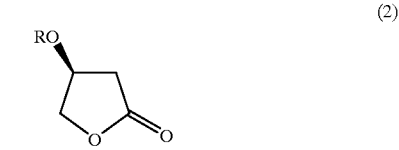
(2)

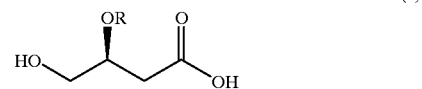
(3)

where R is introduced for the purpose of activating the hydroxy group and can be an alkylsulfonyl, arylsulfonyl, acyl, or phosphoryl group.

The present invention is explained in more detail as set forth hereunder. The present invention relates to the economical and inventive method of preparing highly pure chiral (R)-3,4-epoxybutyric acid and the salt thereof with -high yield by means of inverting the chiral center from (S)-3-activated hydroxybutyrolactone.

The following scheme 1 shows the preparation method of chiral (R)-3,4-epoxybutyric acid and the salt thereof according to this invention:

Scheme 1

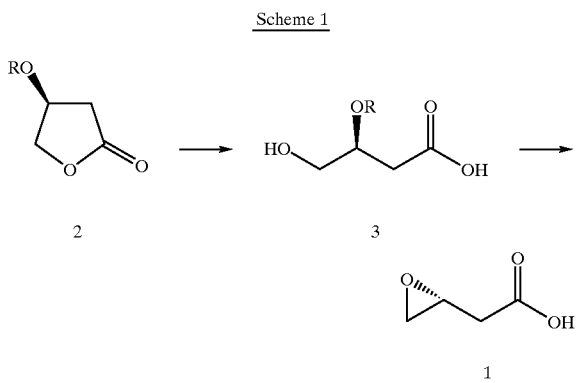

where R is introduced for the purpose of activating the hydroxy group and includes an alkyl, sulfonyl, arylsulfonyl, acyl group, or phosphoryl group.

(S)-3-activated hydroxybutyrolactone of formula 2 as the starting material of the present invention is a compound, which is activated for the purpose of the nucleophilic substitution of the hydroxy group in (S)-3-hydroxybutyrolactone.

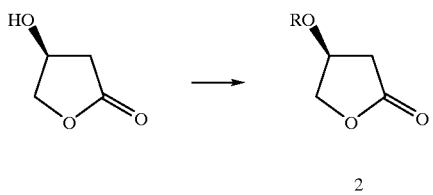

Various chemical methods designed to activate the hydroxy group have been disclosed including sulfonylation, acylation and phosphorylation. Among these methods, the sulfonylation is typically used. The sulfonylation agent includes an alkylsulfonic acid anhydride, alkylsulfonyl chloride or aryisulfonyl chloride. Hence, alkylsulfonyl refers to alkylsulfonyl or haloalkylsulfonyl of $C_{1\sim12}$, or more specifically includes methanesulfonyl, ethanesulfonyl, isopropanesulfonyl, chloromethanesulfonyl, trifluoromethanesulfonyl and chloroethanesulfonyl. Arylsulfonyl includes benzenesulfonyl, toluenesulfonyl, haloarylsulfonyl such as chlorobenzenesulfonyl or bromobenzenesulfonyl, naphthalenesulfonyl, alkoxyarylsulfonyl of $C_{1\sim4}$ such as methoxybenzenesulfonyl and nitroarylsulfonyl. The compound expressed by formula 2, prepared via said activation reaction, includes (S)-3-alkylsulfonylhydroxybutyrolactone, (S)-3-arylsulfonyl hydroxybutyrolactone, and so on. For this purpose, (S)-3-methanesulfonyl hydroxybutyrolactone is generally used.

The first reaction step is a ring-opening reaction of (S)-3-activated hydroxybutyrolactone expressed by formula 2. The ring-opening reaction of this invention is similar to the reaction in which the ester group is hydrolyzed. However, in view of the reaction mechanism, the general hydrolysis method cannot work due to the presence of the 3-activated hydroxy group which is easily detachable at the δ-position of the carbonyl group of the compound of formula 2. In this regard, several commonly known hydrolysis methods have been implemented, but the ring-opening reaction did not occur with respect to the compound of formula 2. Therefore, the target compound of formula 3 under this invention could not be obtained. For example, the hydrolysis of the esters using water as a solvent in the presence of sodium hydroxide is known to be irreversible and quantitative. However, when the ring-opening reaction of 3-methanesulfonylhydroxybutyrolactone was attempted among the compounds of formula 2, the compounds without the sulfonylhydroxy group(-OR) were mainly obtained. In addition to sodium hydroxide, various types of bases (e.g., inorganic bases such as potassium hydroxide, or organic amines such as triethylamine and pyridine) have been used in order to carry out the ring-opening reaction. However, the compounds without the sulfonylhydroxy group(-OR) were obtained as main products instead of the target compound of this invention.

In an effort to examine the effect of (S)-3-activated hydroxy group (—OR) in the above ring-opening reaction, the reaction was carried out with 3-hydroxybutyrolactone with an inactivated hydroxy group under the same reaction conditions. As a result, the target compound of 3,4-hydroxybutyric acid could be quantitatively obtained without dehydration.

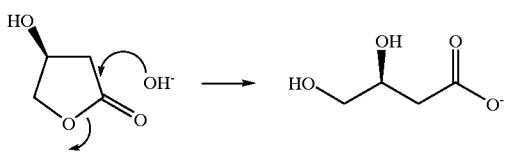

From the above test results, hydrogen at the α-position of (S)-3-activated hydroxybutyrolactone expressed by said formula 2 has higher acidity due to the influence of the carbonyl group. Consequently, the base initially attacks the hydrogen at the α-position prior to its attack on the carbonyl group to give the result of eliminating the sulfonylhydroxy group.

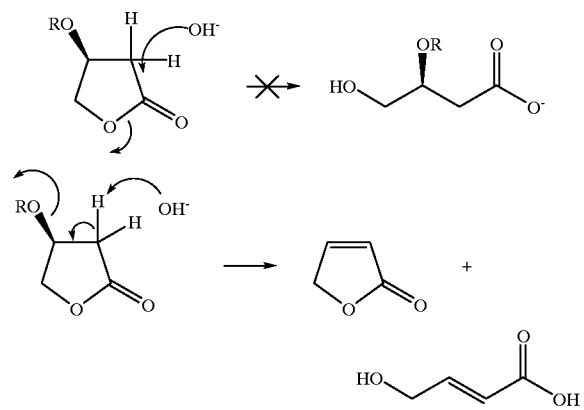

Based on the above results, the ring-opening reaction was attempted in the presence of acid catalyst under the assumption that the hydrogen at the α-position of the carbonyl group may be stabilized without removal in the acidic condition. The acid catalysts include inorganic acids such as sulfuric acid, hydrochloric acid and phosphoric acid, or organic acids such as methanesulfonic acid, toluenesulfonic acid and camphorsulfonic acid. Water is employed as a single solvent in the reaction, but in order to enhance the solubility of (S)-3-activated hydroxybutyrolactone as the starting material, an organic co-solvent with water may be utilized, such as alcohol of $C_{1\sim4}$, tetrahydrofuran, or acetonitrile. It is preferable that the mixing ratio between water and the organic solvent be approximately 95:5(v/v)~50:50 (v/v).

For example, among the compounds under formula 2,3-methanesulfonyl hydroxybutyrolactone was used in the presence of sulfuric acid catalyst of 0.1 equivalent in water as a solvent. Then, the reaction mixture was stirred at 50° C. for 3 hours. The results of nuclear magnetic resonance analysis of the reaction solution confirmed that the target compound of formula 3 was present.

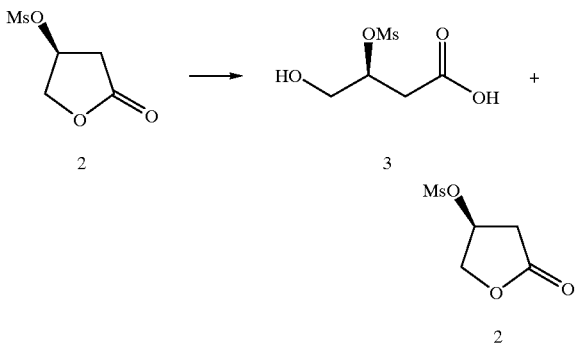

Meanwhile, when the reaction was carried out in the absence of acid catalyst, it was confirmed that a small amount of 3-methanesulfonyl hydroxybutyrolactone was degraded at an early stage of the reaction. Then, methanesulfonic acid was generated therefrom together with furanone without the methanesulfonyl hydroxy group. Methanesulfonic acid, so formed, served as an acid catalyst, and the ring-opening reaction was implemented thereby.

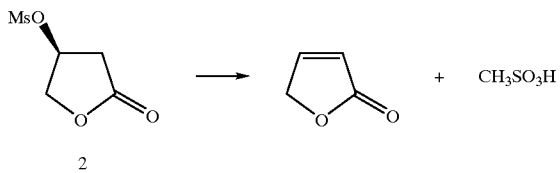

Since the ring-opening reaction is reversible, both the starting material and target ring-opened compound are simultaneously present in the reacting solution. If the solvent is removed for obtaining only the ring-opened compound expressed by formula 3, and the separation of the ring-opened compound is attempted, there is the problem that the ring is closed again to give the result of reverting to the starting material.

With this in mind, the inventors herein have attempted a method of separating and recovering the unreacted starting material through extracting the layer of aqueous solution with an organic solvent. More specifically, the ring-opening reaction of (S)-3-methanesulfonyl hydroxybutyrolactone of formula 2 has been attempted in D$_2$O solution using sulfuric acid as a catalyst. Then, the reaction solution was extracted with CH$_2$Cl$_2$ to recover the unreacted starting material. The test results by the nuclear magnetic resonance analyzer showed that 37 mol % of the compound of formula 2 was contained in the CH$_2$Cl$_2$ solution while 63 mol % of the compound expressed of formula 3 was contained in D$_2$O solution. At the same time, (S)-3-methanesulfonyl hydroxybutyrolactone recovered from the actual reaction was highly pure and could be utilized in the ring-opening reaction without any additional purification process.

The satisfactory results may be produced therefrom since the ring-opened compound expressed by formula 3 is only present in the water layer and not in the organic layer, and vice versa for the unreacted compound expressed by the formula 2. Further, the compound expressed by formula 3, which is present in the water layer, is pure enough to be employed for the next reaction without further purification. It was confirmed that the compound of formula 3 was very stable in the aqueous solution phase, and even after 12 hours of storage at room temperature, recyclization hardly occurred therein.

In addition to the aforementioned dichloromethane, various kinds of solvents, immiscible with water, designed to recover unopened (S)-3-methanesulfonyl hydroxybutyrolactone include the following: haloalkanes such as chloroform, tetrachloromethane, or dichloroethane, aromatic solvents such as benzene, or toluene, ethyl ether, propyl ether, and so on.

As for the next reaction step, the ring-opened compound of formula 3 undergoes an epoxydation reaction in which its chiral center is inversely converted stereoselectively in the presence of a base. Then, the optically pure salt of 3,4-epoxybutyric acid of formula 1 is prepared therefrom. No such reaction has been disclosed in any of the references, and the resulting salt of 3,4-epoxybutyric acid depends on the base used therein.

The inventors of the invention have attempted the inverse conversion reaction of 4-hydroxy-3-activated hydroxybutyric acid of formula 3, so obtained via the ring-opening reaction, by epoxydation in the presence of a base. The aqueous solution of 4-hydroxy-3-methanesulfonyl hydroxybutyric acid, so obtained via the ring-opening reaction, was used. Then, the reaction was carried out in the aqueous solution at room temperature using 2.3 equivalent of sodium hydroxide as a base.

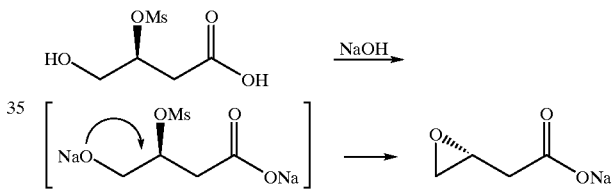

The above reaction showed a remarkable reactivity in view of the fact that the reaction was carried out at room temperature for a short time of less than 30 minutes. When the reacting solution was analyzed by the nuclear magnetic resonance spectrometer, more than 90% conversion rate was duly confirmed. After being acidified, the above solution was extracted with ethyl ether to produce (R)-3,4epoxybutyric acid with a yield of 55%. On the other hand, when (R)-3,4-epoxybutyric acid is used for the preparation of (R)-type derivatives, said derivatives with high yield can be obtained via direct reaction without acidification, extraction and separation, as exemplified by the preparations of various (R)-type derivatives such as (R)4amino-3-hydroxybutiric acid (GABOB), or L-(R)-carnitine in the references.

For the epoxydation reaction according to this invention, an inorganic or organic base may be used. More specifically, applicable bases according to this invention include the following:

Alkali metal hydroxide such as potassium hydroxide, sodium hydroxide, and lithium hydroxide, Alkaline earth metal hydroxide such as magnesium hydroxide, calcium hydroxide and barium hydroxide, Alkali metal alkoxide such as sodium methoxide, sodium ethoxide, sodium t-butoxide, Quaternary ammonium hydroxide such as tetrabutyl ammonium hydroxide, benzyltrimethyl ammonium hydroxide, and Alkylamine such as NR$^1$R$^2$R$^3$ (wherein, R$^1$, R$^2$ and R$^3$ are alkyl groups of C$_{1-7}$, respectively), NHR$^4$R$^5$ (wherein, R$^4$ and R$^5$ are alkyl groups of C$_{2-7}$, respectively) and NH$^2$R$^6$ (wherein, R$^6$ is an alkyl group of C$_{3-9}$), i.e., trimethylamine, triethylamine, tripropylamine, dipropylamine, dibutylamine and t-butylamine.

Meanwhile, the amount of a base may be dependent on the strength or kind of alkalinity, but it is preferable to use the base in the equivalent of 1.0 to 4.0.

Based on the above results, the epoxydation of 4-hydroxy-3-methanesulfonyl hydroxybutyric acid methyl ester having an ester group (not carboxyl group) has been attempted using sodium hydride as a base in tetrahydrofuran. However, the inventors herein have failed to produce the target epoxydated compound while only obtaining compounds without the methanesulfonyl group.

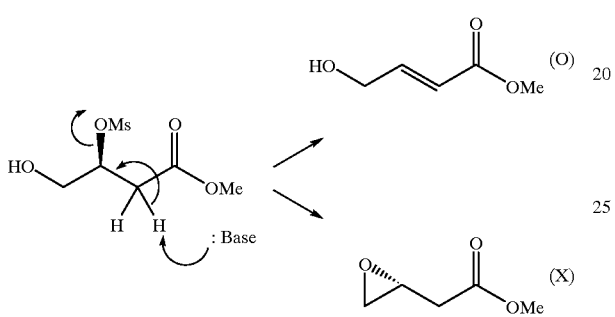

The above results have confirmed that the formation of an anion of the carboxyl group by the treatment of a base is of great importance. In this regard, the hydrogen at the a-position of the carbonyl group may be easily attacked by a base due to its high acidity.

When the carboxyl group of 4-hydroxy-3-methanesulfonyl hydroxybutyric acid is an anion form, the influence of such anion reduces the acidity of the hydrogen at the a -position and consequently makes it difficult for a base to attack. Therefore, the elimination reaction of such methanesulfonyl hydroxy group(-OMs) hardly occurs under said reaction step.

Under the process of preparing chiral 3,4-epoxybutyric acid according to this invention, (S)-3-activated hydroxybutyrolactone of formula 2 as a raw material is used for consecutively carrying out the ring-opening reaction, and inverse conversion reaction of the chiral center by epoxydation. Further, low-priced compounds such as sulfuric acid and sodium hydroxide are used, and continuous reactions are carried out in an aqueous solution in a reactor without a separate purification process. Based on such facts, the above preparation method is expected to be highly useful in the industrial application.

The inverse conversion at the chiral center by epoxydation, one of the pivotal reactions under this invention, is a typical nucleophilic substitution. Based on the characteristics of the chemical reaction, (S)-3,4epoxybutyric acid with an inverted chiral center may be prepared from (R)-3-activated hydroxybutyrolactone as a raw material instead of (S)-3-activated hydroxybutyrolactone.

The present invention is explained in more detail by the following examples but is not limited to these examples.

EXAMPLE 1

Preparation of (S)-3-methane sulfonylhydroxybutyrolactone (S)-3-hydroxy-γ-butyrolactone (10.2 g, 0.10 mol), methanesulfonyl chloride (18.3 g, 0.16 mol) and dichloromethane (100 ml) were placed in a 250 ml reactor. Then, 50% triethylamine-dichloromethane solution (30.4 g, 0.15 mmol) was added dropwise to the mixture at 0° C. for 1 hour. The reacting solution was stirred for 3 hours while maintaining the temperature at 0° C. The solution was extracted with distilled water (100 ml) twice for the removal of the salts therefrom. Dichloromethane solution was dried over magnesium sulfate and filtered. The solvent was slowly concentrated under the reduced pressure to yield the solid thereof. The solid, so formed, was recrystalized with dichloromethane and n-hexane. Then, the crystal was filtered and dried to yield the pure form of (S)-3-methanesulfonyl hydroxybutyrolactone (14.4 g, yield: 80%).

$^1$H-NMR(acetone-d$_6$, ppm): δ 2.7~3.2(m, 2H, —CH$_2$CO—), 3.2(s, 3H, CH$_3$SO$_3$—), 4.5~4.8(m, 2H, O—CH$_2$CH(OMs)—), 5.5~5.6(m. 1H, O—CH$_2$CH(OMs)—)

$^{13}$C-NMR(acetone-d$_6$, ppm): δ 35.31(—CH$_2$CO—), 37.97 (CH$_3$SO$_3$—), 73.41(—CH$_2$CH(OMs)—), 77.39(O—CH$_2$CH(OMs)—), 174.45(—CH$_2$CO—)

EXAMPLE 2

Preparation of (R)-3,4-epoxybutyric acid (S)-3-methanesulfonyl hydroxybutyrolactone (10.0 g, 55.6 mmol), water (100 ml), and the concentrated sulfuric acid (0.549 g, 5.60 mmol) were placed in a 250 ml reactor and stirred at 50° C. for 3 hours. The reacting solution was cooled to room temperature and extracted with dichloromethane (100 ml) twice to recover the unreacted (S)-3-methanesulfonylhydroxybutyrolactone (recovery amount 3.7 g). The target (S)4-hydroxy-3-methanesulfonyl hydroxybutyric acid was present in an aqueous layer.

The aqueous solution of 3N sodium hydroxide (27.1 ml, 81.3 minol) was added to the reacting solution containing said (S)-4-hydroxy-3-methanesulfonyl hydroxybutyric acid (35.0 mmol) and stirred at room temperature for 10 minutes. Onto the reaction solution, the aqueous solution of 1N sulfuric acid was added for acidifying it to pH 3-4, and then the solution was extracted with 100 ml of ethylether for 5 times. The extracting solution was dried with magnesium sulfate, filtered and concentrated under the reduced pressure to yield (R)-3,4-epoxybutyric acid (1.96 g, yield of 55%).

$^1$H-NMR(D$_2$O, ppm): δ 2.3 2.8 (m, 2H, —CH$_2$CO$_2$—H), 2.6 2.9(m, 2H, 4—H), 3.3 3.4 (m, 1H, 3—H), $^{13}$C-NMR(D$_2$O, ppm): δ 37.56(—CH$_2$CO$_2$—H), 49.47(4—CH$_2$), 47.75(3—CH), 175.43(—CO$_2$H),

EXAMPLE 3

Preparation of (S)-4-hydroxy-3-methanesulfonyl hydroxybutyric acid (S)-3-methanesulfonyl hydroxybutyrolactone (1.0 g, 5.6 mmol), D$_2$O (10 ml), and the concentrated sulfuric acid (0.0549 g, 0.56 mmol) were placed in a 25 ml reactor and stirred at 50° C. for 3 hours. The reacting solution was cooled to room temperature and extracted with dichloromethane (10 ml) twice to recover the unreacted (S)-3-methanesulfonyl hydroxybutyrolactone. The presence of the target (S)-4-hydroxy-3-methanesulfonyl hydroxybutyric acid in a pure form in the D$_2$O layer was confirmed by nuclear magnetic resonance.

$^1$H-NMR(D$_2$O, ppm): (2.6~2.8(m, 2H, —CH$_2$CO$_2$H), 3.1(s, OSO$_2$CH$_3$), 3.6~3.9(m, 2H, HOCH$_2$—), 4.9~5.1(m, 1H, —CH(OMs)—)

$^{13}$C-NMR(D$_2$O, ppm): δ 36.27(—CH$_2$CO$_2$H), 38.15 (OSO$_2$CH$_3$), 62.94(—CH(OMs)—), 80.81 (HOCH$_2$—), 174.04(—CH$_2$CO$_2$H)

EXAMPLE 4
Preparation of sodium (R)-3,4-epoxybutyrate

The aqueous solution of 3N sodium hydroxide (2.7 ml, 8.1 mmol) was added to the reacting solution of $D_2O$ containing (S)-4-hydroxy-3-methanesulfonyl hydroxybutyric acid, so prepared from Example 3 and stirred at room temperature for 10 minutes. The presence of the target sodium (R)-3,4-epoxybutyrate in a pure form in the layer of the reacting solution was confirmed by nuclear magnetic resonance.

$^1$H-NMR($D_2O$, ppm): δ 2.3~2.5(m, 2H, $CH_2$—$CO_2Na$), 2.6~2.9(m, 2H), 3.2~3.3(m, 1H)

$^{13}$C-NMR($D_2O$, ppm): δ 40.87(—$CH_2$—$CO_2Na$), 48.24 (4—$CH_2$), 51.08(3—CH), 179.41(—$CO_2Na$)

EXAMPLE 5
Preparation of sodium (R)-3,4-epoxybutyrate

Sodium methoxide (438mg, 8.11 mmol) was added to the reacting solution of $D_2O$ containing (S)4-hydroxy-3-methanesulfonyl hydroxybutyric acid, so prepared from Example 3 and stirred at room temperature for 20 minutes. The presence of the target sodium (R)-3,4-epoxybutyrate in the layer of the reacting solution was confirmed by nuclear magnetic resonance.

$^1$H-NMR($D_2O$, ppm): δ 2.3~2.5(m, 2H, $CH_2$—$CO_2Na$), 2.6~2.9(m, 2H), 3.2~3.3(m, 1H, 3—H)

$^{13}$C-NMR($D_2O$, ppm): (40.89(—$CH_2$—$CO_2Na$), 48.25(4—$CH_2$), 51.10(3—CH), 179.37(—$CO_2Na$)

EXAMPLE 6
Preparation of calcium (R)-3,4-epoxybutyrate

Calcium hydroxide (340mg, 4.59 mmol) was added to the reacting solution of $D_2O$ containing (S)-4-hydroxy-3-methanesulfonyl hydroxybutyric acid, so prepared from the Example 3 and stirred at room temperature for 30 minutes. The presence of the target calcium (R)-3,4-epoxybutyrate in the layer of the reacting solution was confirmed by nuclear magnetic resonance.

1H-NMR($D_2O$, ppm): δ 2.3~2.4(m, 21, $CH_2$—$CO_2Ca$), 2.5~2.8(m, 2H), 3.2~3.3(m, 1H, 3—H)

$^{13}$C-NMR($D_2O$, ppm): δ 40.78(—$CH_2$—$CO_2Ca$), 48.23 (4—$CH_2$), 51.05(3—CH), 179.52(—$CO_2Ca$)

EXAMPLE 7
Preparation of tetrabutyl ammonium (R)-3,4epoxybutyrate 1.0M methanol solution of tetrabutyl ammonium hydroxide (8.12 ml, 8.12 mmol) was added to the reacting solution of $D_2O$ containing (S)-4-hydroxy-3-methanesulfonyl hydroxybutyric acid, so prepared from Example 3 and stirred at room temperature for 30 minutes. The presence of the target tetrabutyl ammonium (R)-3,4-epoxybutyrate in the layer of the reacting solution was confirmed by nuclear magnetic resonance.

$^1$H-NMR($D_2O$, ppm): δ 2.2~2.3(m, 2H, $CH_2$—$CO_2NBu_4$), 2.5~2.8(m, 2H), 3.2~3.3(m, 1H, 3—H)

$^{13}$C-NMR($D_2O$, ppm): δ 41.09(—$CH_2$—$CO_2NBu_4$), 48.23 (4—$CH_2$), 51.14(3—CH), 178.54(—$CO_2NBu_4$)

EXAMPLE 8
Preparation of triethyl ammonium (R)-3,4-epoxybutyrate

Triethylamine (790 mg, 7.81 mmnol) was added to the reacting solution of $D_2O$ containing (S)4-hydroxy-3-methanesulfonyl hydroxybutyric acid, so prepared from Example 3 and stirred at room temperature for 30 minutes. The presence of the target triethyl ammonium (R)-3,4-epoxybutyrate in the layer of the reacting solution was confirmed by nuclear magnetic resonance.

$^1$H-NMR($D_2O$, ppm): δ 2.2~2.4(m, 2H, $CH_2$—$CO_2HNEt_3$), 2.5~2.8(m, 2H), 3.1~3.2(m, 1H, 3—H)

$^{13}$C-NMR($D_2O$, ppm): δ 40.94(—$CH_2$—$CO_2HNEt_3$), 48.15 (4—$CH_2$), 51.04(3—CH), 178.97(—$CO_2HNEt_3$)

EXAMPLE 9
Preparation of diisopropyl ammonium (R)-3,4epoxybutyrate

Diisopropyl amine (790 mg, 7.81 nmmol) was added to the reacting solution of $D_2O$ containing (S)4-hydroxy-3-methanesulfonyl hydroxybutyric acid, so prepared from Example 3 and stirred at room temperature for 2 hours. The presence of the target diisopropyl ammonium (R)-3,4-epoxybutyrate in the layer of the reacting solution was confirmed by nuclear magnetic resonance.

$^1$H-NMR($D_2O$, ppm): δ 2.2~2.4(m, 2H, $CH_2$—$CO_2HN(H)Pr^i_2$), 2.5~2.8(m, 2H), 3.1~3.2(m, 1H, 3—H)

13C-NMR($D_2O$, ppm): δ 40.92(—$CH_2$—$CO_2HN(H)Pr^i_2$), 48.12(4$CH_2$), 51.02(3—CH), 178.95(—$CO_2HN(H)Pr^i_2$)

EXAMPLE 10
Preparation of t-butyl ammonium (R)-3,4epoxybutyrate t-butyl amine (571mg, 7.81mmol) was added to the reacting solution of $D_2O$ containing (S)-4-hydroxy-3-methanesulfonyl hydroxybutyric acid, so prepared from Example 3 and stirred at room temperature for 4 hours. The presence of the target t-butyl anmmonium (R)-3,4-epoxybutyrate in a layer of the reacting solution was confirmed by nuclear magnetic resonance.

$^1$H-NMR($D_2O$, ppm): a 2.1~2.4(m, 2H, $CH_2$—$CO_2HNH_2Bu^t$), 2.5~2.8(m, 2H), 3.1~3.2(m, 1H, 3—H)

$^{13}$C-NMR($D_2O$, ppm): δ 40.88(—$CH_2$—$CO_2HNH_2Bu^t$), 48.13(4—$CH_2$), 51.01(3—CH), 179.10(—$CO_2HNH_2Bu^t$)

The process of preparing chiral 3,4-epoxybutyric acid and the salt thereof according to this invention may be very useful in an industrial scale in that a) inexpensive compounds are utilized in aqueous solution, and b) the reactions in a reactor can be continuously carried out.

What is claimed is:

1. A process of preparing chiral 3,4-epoxybutyric acid of the following formula 1 and the salt thereof, wherein
   (S)-3-activated hydroxybutyrolactone of the following formula 2 is subjected to a ring-opening reaction in an aqueous solvent, 4-hydroxy-3-activated hydroxybutyric acid of the following formula 3 is prepared therefrom, and
   4-hydroxy-3-activated hydroxybutyric acid of said formula 3 is subjected to an inversion of the chiral center by epoxydation in the presence of a base in order to prepare 3,4-epoxybutyric acid of the following formula 1

(1)

(2)

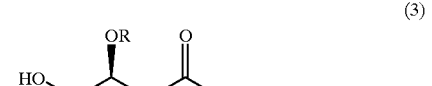
(3)

where R is an alkylsulfonyl, arylsulfonyl, acyl group, or phosphoryl group.

2. A process of preparing chiral 3,4-epoxybutyric acid and the salt thereof according to claim 1, wherein said R is selected from the following groups: $C_{1-12}$ alkylsulfonyl group, $C_{1-12}$ or haloalkylsulfonyl group, benzenesulfonyl group, toluenesulfonyl group, halobenzenesulfonyl group, naphthalene sulfonyl group, alkoxy benzenesulfonyl group and nitrobenzenesulfonyl group.

3. A process of preparing chiral 3,4-epoxybutyric acid and the salt thereof according to claim 2, wherein said R is a methanesulfonyl group.

4. A process of preparing chiral 3,4-epoxybutyric acid and the salt thereof according to claim 1, wherein said ring-opening reaction is carried out in the presence of water as a single solvent or a co-solvent containing water and an organic solvent.

5. A process of preparing chiral 3,4-epoxybutyric acid and the salt thereof according to claim 4, wherein said organic solvent is selected from a $C_{1-14}$ alcohol, tetrahydrofuran and acetonitrile.

6. A process of preparing chiral 3,4-epoxybutyric acid and the salt thereof according to claim 1 or 4, wherein said ring-opening reaction is carried out in the presence of an acid catalyst.

7. A process of preparing chiral 3,4epoxybutyric acid and the salt thereof according to claim 6, wherein said acid catalyst is selected from sulfuric acid, hydrochloric acid, phosphoric acid, methanesulfonic acid, toluenesulfonic acid and camphorsulfonic acid.

8. A process of preparing chiral 3,4epoxybutyric acid and the salt thereof according to claim 1, wherein said epoxydation reaction is carried out in the presence of a base, which is selected from alkali metal hydroxide, alkaline earth metal hydroxide, alkali metal alkoxide and quaternary ammonium hydroxide.

9. A process of preparing chiral 3,4-epoxybutyric acid and the salt thereof according to claim 8, wherein said alkali metal hydroxide is selected from sodium hydroxide, potassium hydroxide and lithium hydroxide.

10. A process of preparing chiral 3,4-epoxybutyric acid and the salt thereof according to claim 8, wherein said alkaline earth metal hydroxide is selected from magnesium hydroxide, calcium hydroxide and barium hydroxide.

11. A process of preparing chiral 3,4-epoxybutyric acid and the salt thereof according to claim 8, wherein said alkali metal alkoxide is selected from sodium methoxide, sodium ethoxide and sodium t-butoxide.

12. A process of preparing chiral 3,4-epoxybutyric acid and the salt thereof according to claim 8, wherein said quaternary ammonium hydroxide is selected from tetrabutyl ammonium hydroxide and benzyltrimethyl ammonium hydroxide.

13. A process of preparing chiral 3,4-epoxybutyric acid and the salt thereof according to claim 1, wherein said epoxydation reaction is carried out in the presence of an alkylamidne base.

14. A process of preparing chiral 3,4-epoxybutyric acid and the salt thereof according to claim 13, wherein said alkylamine is $NR^1R^2R^3$, wherein, $R^1$, $R^2$ and $R^3$ are $C_{1-7}$ alkyl groups.

15. A process of preparing chiral 3,4-epoxybutyric acid and the salt thereof according to claim 13, wherein said alkylamine is $NHR^4R^5$, wherein, $R^4$ and $R^5$ are $C_{2-7}$ alkyl groups.

16. A process of preparing chiral 3,4-epoxybutyric acid and the salt thereof according to claim 13, wherein said alkylamine is $NH2R^6$, wherein, $R^6$ is a $C_{3-9}$ alkyl group.

17. A process of preparing chiral 3,4-epoxybutyric acid and the salt thereof according to claim 8 or 13, wherein said base is employed in the equivalent ratio of 1.0~4.0.

18. A process of preparing chiral 3,4-epoxybutyric acid and the salt thereof according to claim 8 or 13, wherein the salt thereof is determined by the base used in the epoxydation reaction therein.

* * * * *

UNITED STATES PATENT AND TRADEMARK OFFICE
CERTIFICATE OF CORRECTION

PATENT NO.    : 6,232,478 B1
DATED         : May 15, 2001
INVENTOR(S)   : Il Suk Byun et al.

It is certified that error appears in the above-identified patent and that said Letters Patent is hereby corrected as shown below:

<u>Title page,</u>
Delete Item [76] in its entirety and then substitute therefore:
-- [75] Inventors: Il Suk Byun, Taejeon; Kyung Il Kim, Taejeon; Yoon Hwan Choi, Kyungki-do, all of Korea (KR) --.

Insert -- [73] Assignee: Samsung Fine Chemicals Co., Ltd. (KR) --

<u>Column 12,</u>
Line 29, "NH2R$^6$" should read -- NH$_2$R$^6$ --.

Signed and Sealed this

Sixth Day of August, 2002

Attest:

Attesting Officer

JAMES E. ROGAN
*Director of the United States Patent and Trademark Office*